United States Patent
Lee et al.

(10) Patent No.: US 10,203,313 B2
(45) Date of Patent: Feb. 12, 2019

(54) HYDROGEN SENSOR AND SENSOR CIRCUIT

(71) Applicant: Industry-Academic Cooperation Foundation, Yonsei University, Seoul (KR)

(72) Inventors: WooYoung Lee, Seoul (KR); Seongil Im, Seoul (KR); YoungTack Lee, Seoul (KR); HwaeBong Jung, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 237 days.

(21) Appl. No.: 14/501,036

(22) Filed: Sep. 30, 2014

(65) Prior Publication Data
US 2015/0233878 A1    Aug. 20, 2015

(30) Foreign Application Priority Data
Feb. 18, 2014   (KR) .................. 10-2014-0018236

(51) Int. Cl.
  *G01N 33/00*  (2006.01)
  *H01L 29/786*  (2006.01)
  *G01K 7/01*  (2006.01)

(52) U.S. Cl.
  CPC .......... *G01N 33/005* (2013.01); *G01K 7/015* (2013.01); *G01N 33/0036* (2013.01); *H01L 29/786* (2013.01); *H01L 29/78693* (2013.01)

(58) Field of Classification Search
  CPC ... H01L 29/786; H01L 29/772; G01N 33/005; G01N 33/0036; G01N 27/416; G01K 7/015; H03M 1/124
  See application file for complete search history.

(56) References Cited

U.S. PATENT DOCUMENTS

| 6,294,133 B1 * | 9/2001 | Sawada | G01K 7/015 204/400 |
| 2005/0167573 A1 * | 8/2005 | Maruyama | H01L 27/1214 250/214.1 |
| 2011/0259083 A1 * | 10/2011 | Lee | G01N 27/127 73/31.05 |
| 2013/0181854 A1 * | 7/2013 | Koyama | G11C 27/026 341/122 |

FOREIGN PATENT DOCUMENTS

| KR | 10-2007-0121761 | 12/2007 |
| KR | 20110075841 | 7/2011 |
| KR | 10-2013-0125183 | 11/2013 |

OTHER PUBLICATIONS

Young Tack Lee et al, "Sensing extremely limited H2 contents by Pd nanogap connected to an amorphous InGaZnO thin-film transistor†" , The Royal Society of Chemistry 2013 Nanoscale, Jul. 2013. 8915-8920, Yonsei University, Seoul 120-749, Korea.

* cited by examiner

Primary Examiner — Jennifer E Simmons
Assistant Examiner — Quang X Nguyen

(57) ABSTRACT

A hydrogen sensor includes a hydrogen-sensing unit and a transistor connected to the hydrogen-sensing unit. The hydrogen-sensing unit includes a substrate made of an elastic material, a thin film made of transition metal or alloy thereof, disposed on the surface of the substrate and having a plurality of nanogaps formed therein, and an electrode formed on the thin film. The hydrogen-sensing unit is connected with a source (or drain) or a gate of the transistor via a connector.

5 Claims, 7 Drawing Sheets

Inverter-type (a)

Gate-type (b)

Hybrid-type (c)

Inverter-type

(a)

Gate-type

(b)

Hybrid-type

(c)

HYDROGEN SENSOR AND SENSOR CIRCUIT

BACKGROUND OF THE INVENTION

Field of the Invention

The present invention relates, in general, to a hydrogen sensor.

Description of the Related Art

Generally, hydrogen energy has been actively studied since it is reusable and has an advantage in that it does not induce environmental pollution.

However, since hydrogen gas runs the risk of explosion if exposed to air by 4% or more, it is difficult to widely apply hydrogen gas in our real life if safety-in-use is not secured. Therefore, along with the studies on utilization of hydrogen energy, a hydrogen gas-detection sensor (simply referred hereinafter to as a 'hydrogen sensor') has been developed in order to, in practical use, detect leakage of the hydrogen gas in early stages.

In the meantime, as hydrogen energy is availably commercialized, it is expected to be first applied to the automobile markets. Considering that researches are currently carried out on loading compressed hydrogen gas on an automobile, there is a need to develop a hydrogen safety sensor that can be adapted to a fuel supply and an electronic unit so as to detect leakage of hydrogen. Further, the hydrogen sensor is essentially required for the detection of leakage of hydrogen, monitoring of a hydrogen concentration, or the like, as a component of hydrogen storage and supply systems in a hydrogen fuel cell-activated unit. In addition, a hydrogen sensor is often used to detect a gas-leaking portion using hydrogen gas, rather than conventionally using helium gas, in an air-conditioner, refrigerator or the like, which uses a coolant, in order for more precise detection.

In regard to such a hydrogen sensor, a hydrogen sensor is known in which a Pd thin film (TF) or Pd alloy TF is disposed on an elastic substrate, and nanogaps are formed in the TF by extension of the substrate, and hydrogen is detected using the nanogaps (see Korean Patent Registration No. 10-1067557). However, such a hydrogen sensor is the type of sensor that detects hydrogen using a change in current, so a signal from the sensor can be recognized only when the hydrogen sensor is coupled to a computer or the like and electric current detected from the hydrogen sensor is converted into a voltage. A conventional hydrogen sensor, however, has a problem of a low current signal. That is, a specific reference voltage is required in order to check whether a voltage signal indicates an ON or OFF state. However, in a conventional hydrogen sensor, a current signal induced from a low hydrogen concentration is so low that, even when converted into a voltage signal, it is difficult to check whether the converted voltage signal indicates an ON or OFF signal.

SUMMARY OF THE INVENTION

Accordingly, the present invention has been made keeping in mind the above problems occurring in the related art, and an object of the present invention is to provide a hydrogen sensor capable of easily and rapidly detecting a low concentration of hydrogen.

In order to achieve the above object, according to one aspect of the present invention, there is provided a hydrogen sensor including: a hydrogen-sensing unit; and a transistor connected to the hydrogen-sensing unit, wherein the hydrogen-sensing unit includes: a substrate made of an elastic material; a thin film made of transition metal or alloy thereof, disposed on a surface of the substrate and having a plurality of nanogaps formed therein; and an electrode formed on the thin film, wherein the hydrogen-sensing unit is connected with a source (or drain) or a gate of the transistor via a connector.

In an embodiment, the transistor may be a thin film transistor (TFT).

In an embodiment, the TFT may be an a-IGZO TFT.

In an embodiment, the hydrogen-sensing unit may be connected to a source (or drain) of the transistor to form an inverter-type hydrogen sensor, whereby a change in current induced from a concentration of hydrogen, which is detected via the hydrogen-sensing unit, is converted into an ON-OFF type voltage signal via the transistor.

In an embodiment, the hydrogen-sensing unit may be connected to a gate of the transistor to form a gate-type hydrogen sensor, whereby the hydrogen-sensing unit serves as an accumulator.

In accordance with another aspect of the present invention, there is provided a hydrogen sensor including: a hydrogen-sensing unit; and a transistor connected to the hydrogen-sensing unit, wherein the hydrogen-sensing unit includes: a substrate made of an elastic material; a thin film bade of transition metal or alloy thereof, disposed on a surface of the substrate and having a plurality of nanogaps formed therein; and an electrode formed on the thin film, wherein the hydrogen sensor forms a hybrid-type hydrogen sensor consisting of an inverter-type hydrogen sensor, in which the hydrogen-sensing unit is connected to a source (or drain) of the transistor, and a gate-type hydrogen sensor, in which the hydrogen-sensing unit is connected to a gate of the transistor.

In an embodiment, the transistor may be a thin film transistor (TFT).

In an embodiment, the TFT may be an a-IGZO TFT.

In an embodiment, a change in current induced from a concentration of hydrogen, which is detected via the gate-type hydrogen sensor, is converted into an ON-OFF type voltage signal via the transistor of the inverter-type hydrogen sensor.

In accordance with a further aspect of the present invention, there is provided a hydrogen sensor including: a hydrogen-sensing unit; and a resistor connected to the hydrogen-sensing unit, wherein the resistor serves to detect a change in output from the hydrogen-sensing unit.

According to the present invention, the hydrogen-sensing unit is connected to the transistor or resistor, so it is possible to detect a lower concentration of hydrogen.

BRIEF DESCRIPTION OF THE DRAWINGS

The above and other objects, features and advantages of the present invention will be more clearly understood from the following detailed description when taken in conjunction with the accompanying drawings, in which.

DETAILED DESCRIPTION OF THE INVENTION

Hereinbelow, preferred embodiments of the present invention will be described in detail with reference to the accompanying drawings. In the description, well-known technologies in the art will be omitted. Although such a description is omitted, persons skilled in the art, however, will appreciate characteristic features of the present invention when reading and understanding the following description.

As described in detail below, the present invention proposes a hydrogen sensor system in which the hydrogen sensing capability of a nanogap-based Pd sensor is improved by connecting the Pd sensor to an electrically stable amorphous InGaZnO thin-film transistor (a-IGZO TFT) in two different ways: Pd connection to the TFT source and to the gate. In one embodiment, the IGZO TFT is chosen, since it is stable enough to bear the gate bias stress during hydrogen detection; it would eventually be integrated with the present Pd sensor. As a result of the Pd connection to the TFT source, the present sensor circuit greatly enhances the hydrogen-induced signal by three orders of magnitude in the sense of output voltage, clearly resolving a minimum hydrogen concentration of 0.05%. When the nanogap-based Pd sensor is connected to the TFT gate, an even lower hydrogen concentration of less than 0.05% is visibly detected.

Figure 1:
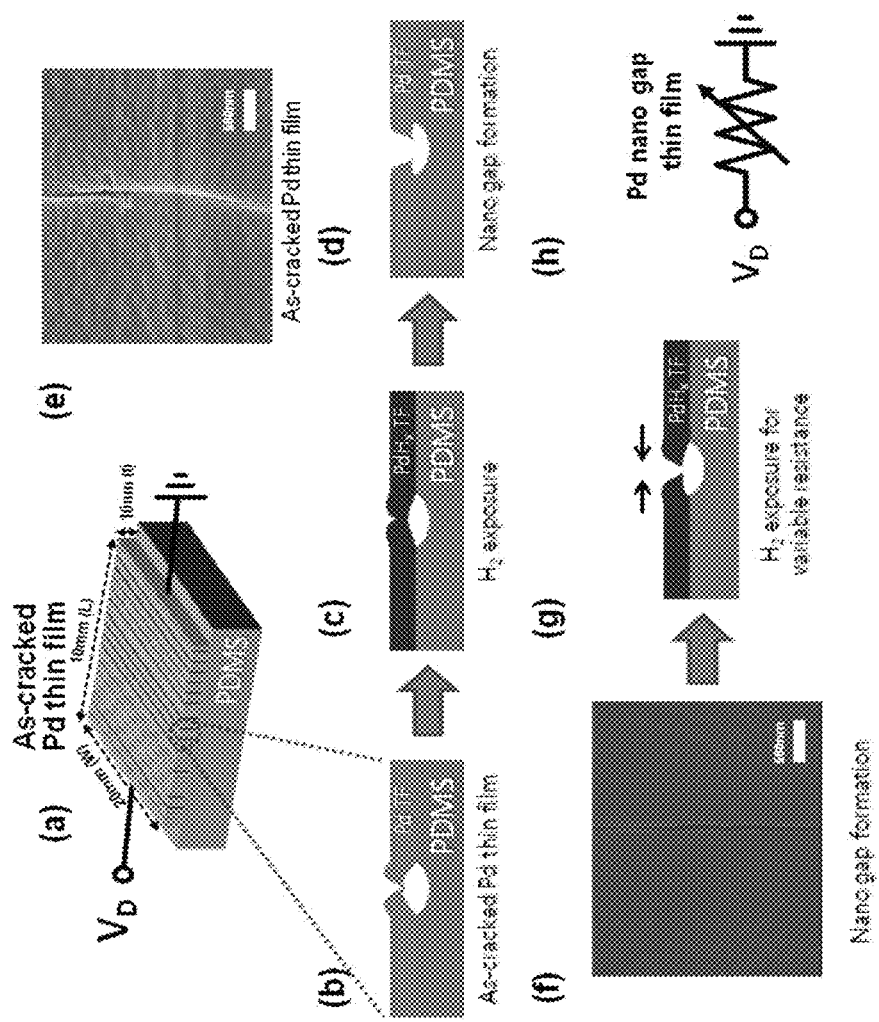
FIG. 1 is a schematic diagram showing a hydrogen sensor adapted to a hydrogen sensor system according to an embodiment of the present invention.

Polydimethylsiloxane (PDMS) elastomer was used as the substrate of the hydrogen gas sensor, to create nanocracks (or nanogap stripes) in the Pd thin-film (TF). The base resin (Sylgard 184, Dow Corning) was mixed with a curing agent at a volume ratio of 10:1 and was kept in the vacuum chamber for 10 min to evacuate any air bubbles. Then, the PDMS mixture was cured for 30 min on a hotplate at 423 K. In order to fabricate the hydrogen gas sensor, a 10 nm-Pd thin film was deposited on the PDMS substrate by using a DC magnetron sputtering system. After Pd deposition, the Pd-PDMS substrate was mounted onto a stretching machine and nanocracks were created under a tensile stress. FIG. 1(a) shows a schematic of the as-cracked Pd TF device (area dimension: 10 mm [L]×20 mm [W]), where many nanogap stripes are shown and one of them is illustrated in FIG. 1(b) with its schematic cross section. The single nanocrack appears deformed but yet maintains an internal connection (the connection was confirmed by an electric conduction measurement). However, if the initially cracked region comes into contact with hydrogen gas molecules (i.e. is exposed to hydrogen to form a PdHx compound; FIG. 1(c)) and the molecules are evacuated, the crack is eternally open with a nanogap as shown in FIG. 1(d). FIGS. 1(e) and 1(f) are the respective scanning electron microscopy (SEM) images of as-cracked and eternal nanogap-containing Pd TF. According to the SEM images, the as-cracked Pd still shows a physical contact between the two Pd regions around the crack stripe while the other stripe from nanogap-containing Pd shows about 50 nm separation (gap distance), although the distance is not uniform. Based on the structure of FIGS. 1(d) and (f), the nanogap Pd TF now operates as a hydrogen sensor, since ON/OFF (contact/noncontact) switching takes place in the Pd TF with variable resistances according to the degree of hydrogen molecule adsorption on the Pd surface or hydrogen reaction with Pd. The hydrogen-adsorbed Pd TF changes its phase to PdHx with an expanded volume which leads to a physical contact in the nanogap. As a result, the variable electrical conductance of nanogap Pd TF may indicate hydrogen concentration. In the meantime, a method of forming such a Pd nanogap TF, a method of fabricating a hydrogen sensor system using the former method, and the like are disclosed in e.g. Korean Patent Registration No. 10-1067557, the contents of which are incorporated herein by reference.

The structure of a-IGZO TFTs adapted to an embodiment of the present invention is an inverted-stagger type with a width-to-length (W/L) ratio of 100:10 mm using a bottom gate. A 300 nm-thick $SiO_2$ gate insulator layer was deposited on the patterned Cu-MoTi gate electrode by a plasma-enhanced chemical vapor deposition (PECVD) system. Then, a 60 nm-thick active channel layer (a-IGZO) was deposited by a DC magnetron sputtering system. The formation of the $SiO_2$ etch stopper (75 nm) and Mo source/drain electrodes were sequentially performed, followed by the formation of a 300 nm thick PECVD $SiO_2$ passivation layer. All the patterning processes were carried out by photolithography that involved wet chemical etching and PECVD processes. The device annealing at 300° C. in ambient air was performed as a final process. Like this, a method of fabricating such an inverter-type TFT, the structure, the function and the like of the same are already well known in the art, so the detailed description thereof will be omitted.

Figure 2:
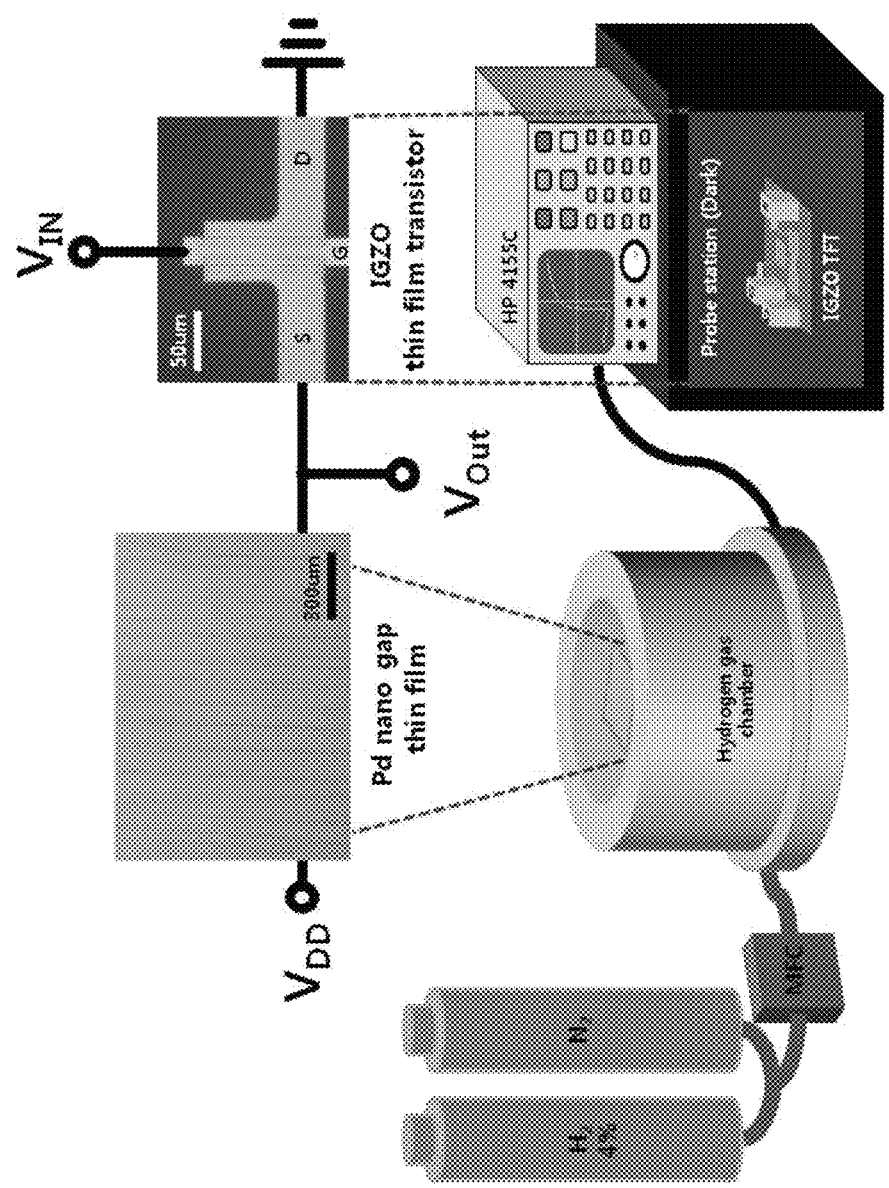
FIG. 2 is a schematic diagram showing a hydrogen sensor system according to an embodiment of the present invention.

FIG. 2 shows a schematic diagram of our hydrogen sensor system, which consists of a small gas chamber with a volume of about 250 ml and a mass flow controller (MFC) for pure 100% $N_2$ (for purging) and 96% $N_2$+4% hydrogen mixture gas (for sensing). The pressure in the chamber was maintained at 1 atm at room temperature. The nanogap Pd TF device was mounted in the gas chamber and connected to an electrically stable a-IGZO TFT device (to the source electrode) of a probe station in the dark. Supply and input voltages ($V_{DD}$ and $V_{IN}$) were applied by a semiconductor parameter analyzer (Model HP 4155C, Agilent Technologies). Output voltage ($V_{OUT}$) according to hydrogen sensing was also measured by the semiconductor analyzer. The circuit illustration in FIG. 2 contains the top view images of the present nanogap Pd TF device and a-IGZO TFT, which were obtained from an optical microscope. As shown, the present Pd TF contains many nanogap stripes, of which the number was approximated to be 60-70. The present measurement setup is analogous to a logic inverter circuit for digital output, except that ours has a variable resistor composed of a hydrogen-sensing nanogap Pd TF instead of a constant load resistor (the connection type shown in FIG. 2 will be referred to as an 'inverter-type connection'). The inventors could thus expect that small hydrogen-induced analogue current would be properly amplified in voltage signals.

Figure 3:
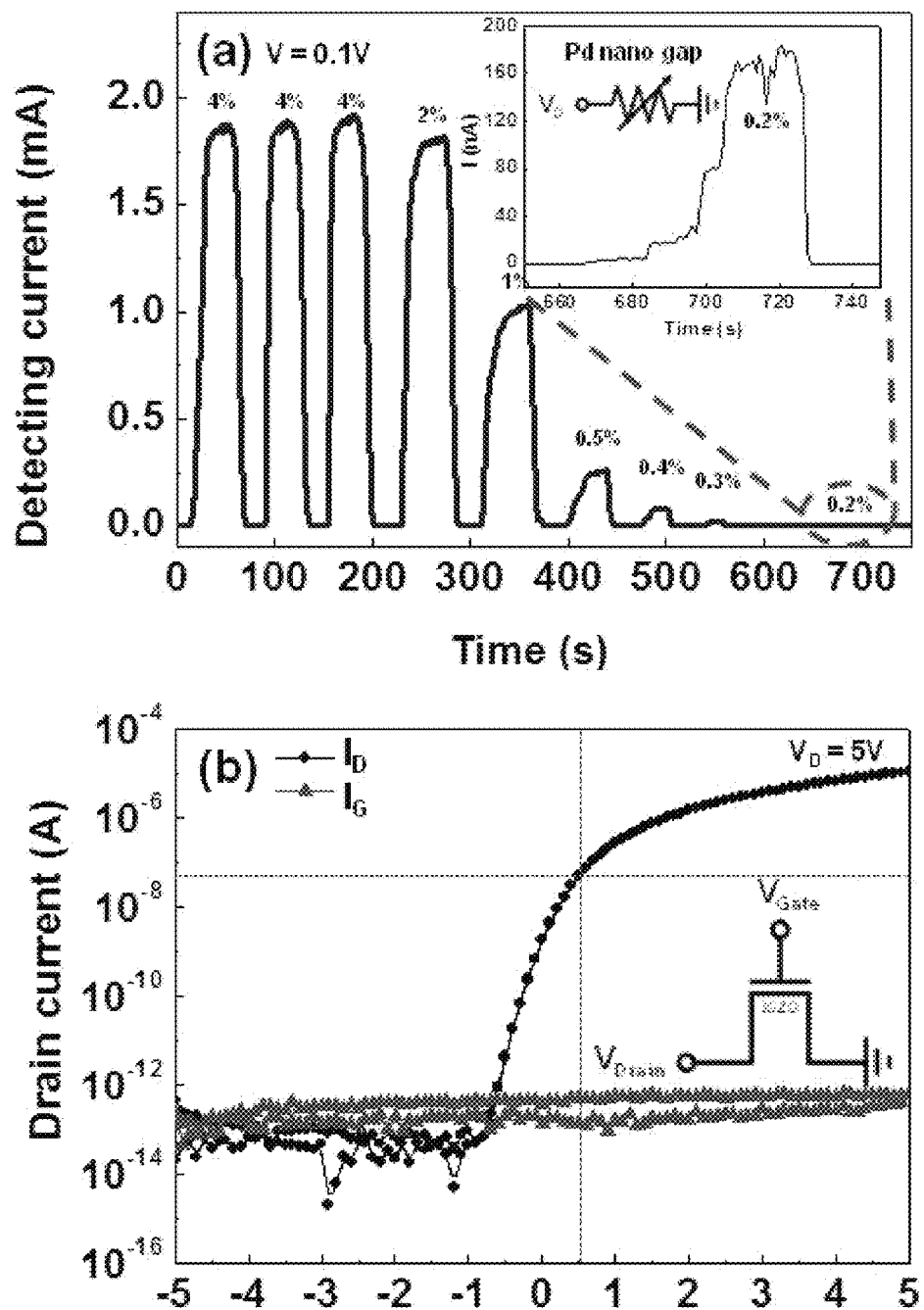
FIG. 3 shows a detecting current-time plot obtained by the hydrogen sensor exposed with various hydrogen concentrations, and drain current-gate voltage transfer characteristics of a-IGZO TFT device.

FIG. 3a is a detecting current vs. time plot which is obtained from our nanogap Pd TF (under 0.1 V) by hydrogen gas-controlled ON/OFF switching. Various hydrogen ambiences of 4%, 2%, 1%, 0.5%, 0.4%, 0.3%, and 0.2% (as mixed with pure $N_2$) were exposed to the Pd sensor. While hydrogen concentrations higher than 0.3% were quite nicely detected at the current range from 2 mA to few hundred mA, it was not easy to note a lower hydrogen concentration from the current signal. In particular, 0.2% hydrogen was barely sensed and noted only by magnifying the sensing signal (about 200 nA) as shown in the inset of FIG. 3(a). Worse than that, sensing (and recovery) time gets longer with smaller hydrogen concentration, so that detecting 0.3% hydrogen appeared to take more than 20 seconds. Hence, the present invention employed an electrically stable a-IGZO TFT to amplify the sensing signal and simultaneously to shorten the sensing time, converting the output signal from current to voltage. FIG. 3(b) is the drain current-gate voltage ($I_D$-$V_G$) transfer characteristics of the present oxide TFT along with gate leakage current ($I_G$) curves, as obtained under a drain bias of $V_D$=5 V. As shown in the TFT transfer curves of FIG. 3(b), the present TFT was very stable with 0.1 pA $I_G$ leakage and without any gate hysteresis, turning on above 0 V (ON/OFF ratio was more than about $10^8$ and the saturation field effect mobility was about 10 $cm^2V^{-1}s^{-1}$). Since the transistor $I_D$ current covers a broad range from 20 µA to 0.1 pA while our Pd sensor has another current range from 2 mA to a few hundred nA, some reasonable $V_{OUT}$ signals are expected through an overlapped current region when these two devices are connected in series.

Figure 4:
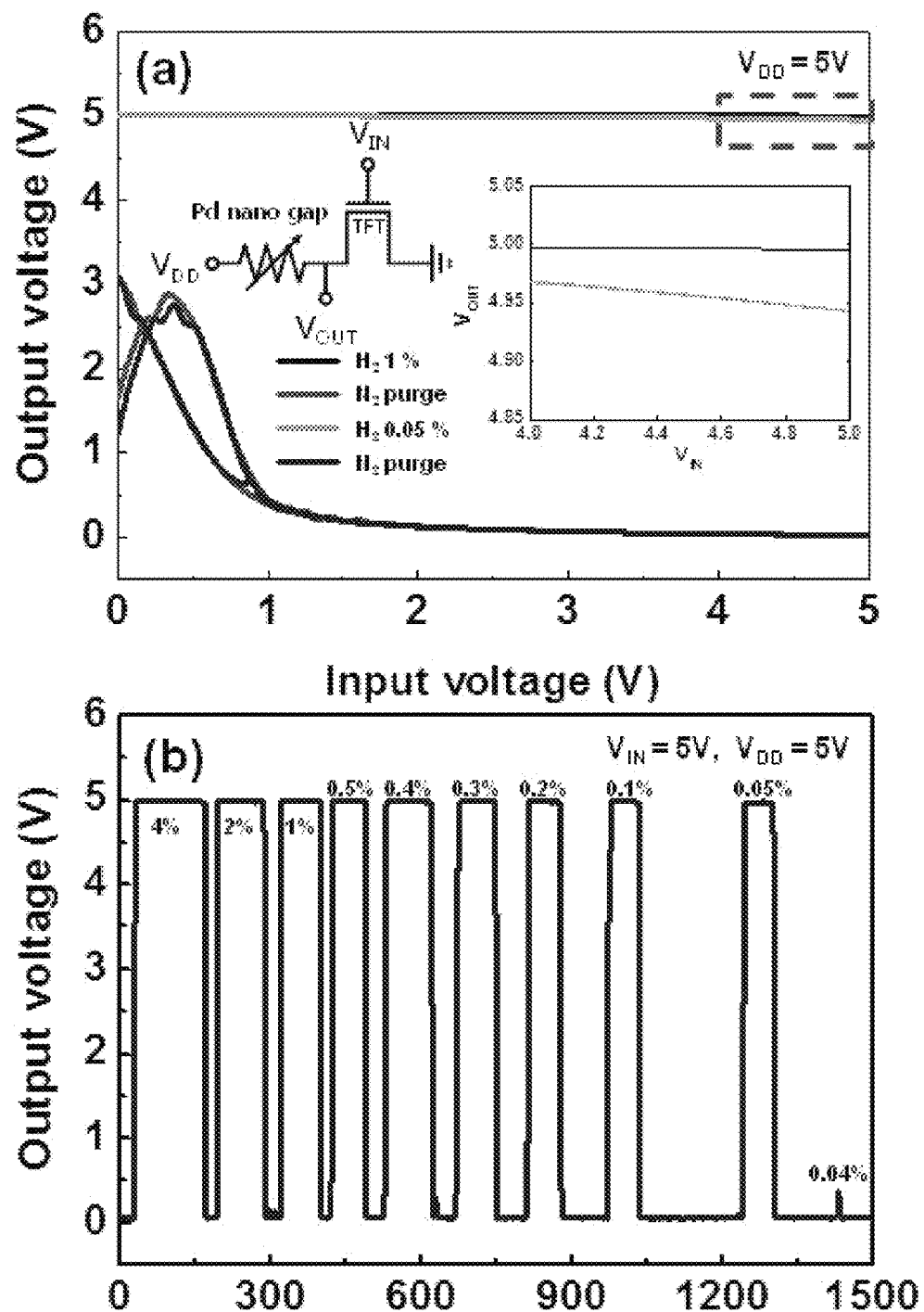
FIG. 4 shows a $V_{OUT}$-$V_{IN}$ plot obtained by an inverter-type hydrogen sensor system tested for various hydrogen concentrations, and an output voltage-time plot for various hydrogen concentrations.

The series connection scheme has already been introduced in FIG. 2 and is now shown in the inset circuit diagram of FIG. 4(a), where $V_{OUT}$ vs. $V_{IN}$ plots are displayed as the main measurement results. For hydrogen detection experiments, hydrogen gas of 1%, 0.05%, and 0% (purged with 100% $N_2$ gas) was infused into the hydrogen sense chamber of FIG. 2 in the following sequence: initial 1% hydrogen infusion, $N_2$ purge, 0.05% hydrogen infusion, and final $N_2$ purge, so that each $V_{OUT}$ curve could be obtained under a $V_{DD}$ of 5 V as shown in FIG. 4a. According to the plots, the $V_{OUT}$ for 0.05% hydrogen detection appears almost the same as that for 1% hydrogen sensing, indicating almost 5 V; this result is confirmed by magnifying some part of the plot (see the inset plot for a range of $V_{IN}$=4~5 V). Based on these $V_{OUT}$-$V_{IN}$ plots, the present invention implemented a time domain hydrogen detection experiment (for VOUT vs. time plot), dynamically varying the hydrogen concentration from 4% to 0.04% under a fixed voltage condition of $V_{DD}$=$V_{IN}$=5 V. FIG. 4(b) displays the dynamic hydrogen detection plot in time domain, where the detection voltage $V_{OUT}$ appears to be about 5 V for all the cases from 4% to 0.05% hydrogen, as predicted by the results from FIG. 4(a). The detection voltage abruptly decreases to 0.4 V from about 5 V when the hydrogen concentration further decreases to 0.04%, although this specific result was actually irreproducible unlike the case of 0.05% and higher hydrogen percentages. It is thus recognized that the series connection setup for hydrogen sensing still has its own detection limit at 0.05%. In spite of such a limitation, however, it is acknowledgeable that applying the present logic inverter type circuit to the analogue nanogap Pd TF remarkably enhances the visibility of the low % hydrogen signal by a few orders of magnitude and simultaneously shortens the sensing (and recovery) time to 1~2 seconds as shown in FIG. 3(a), the detected current at 4% hydrogen-exposure was about 2.0 mA, and the current detected at 0.3% hydrogen-exposure was about 0.2 mA, whereas in the case of an inverter-type sensor, at 4% and 0.2% hydrogen, the detected $V_{OUT}$ was kept substantially constant. Further, for reaction time, it was confirmed that in the case of inverter-type, $V_{OUT}$ changed vertically). This is a meaningful result. In fact, the electrical conductance or conducting path in nanogap Pd film still exists even with the low 0.05% hydrogen molecules, but is too small to measure/or estimate and thus becomes visible only with the connection to a transistor. Apparent electrical disconnection in the nanogap Pd film is eventually observed with an extremely low % of hydrogen molecules (here 0.04% is the onset point of the open circuit).

Complete gap opening might take place in single or a few nanogap stripes at a certain point of dilute ambient hydrogen, leading to an abrupt disconnection. In this event, our nanogap-containing Pd TF has then a charge capacitance due to the gap distance. The gap distance would be so dependent on the hydrogen concentration that we may estimate an extremely low % of hydrogen by introducing the capacitance of the nanogap Pd TF to the gate of the same a-IGZO TFT with a dielectric oxide (300 nm thick $SiO_2$). Such a capacitor-induced circuit is shown in the inset of FIG. 5(a) and the transfer curves have been accordingly obtained from the circuit with the oxide TFT and Pd TF variable capacitor under two ambient conditions of 0.04% and 0% hydrogen. The initial transfer curve was obtained as a reference from the TFT alone. Connected in series to the Pd TF, the total gate capacitance ($C_{total}$) of the inset circuit should become smaller than the dielectric oxide capacitance ($C_{ox}$) because a nanogap-induced capacitance ($C_{gap}$) should be also considered as shown below in Equation (1).

$$C_{total} = \frac{1}{\frac{1}{C_{gap}} + \frac{1}{C_{ox}}} \quad \text{Equation (1)}$$

The smaller $C_{total}$ leads to a slightly smaller $I_D$ current than that by $C_{ox}$ alone at an identical ON-state $V_G$ (e.g. 3 V), as shown in FIG. 5(a). Simultaneously, at the same OFF-state $I_D$ (e.g. about 0.3 pA), the smaller $C_{total}$ leads to a more negative $V_G$, that is, the transfer curves of the TFT with the Pd TF capacitor shows more negatively shifted $V_G$ with a lower hydrogen concentration, since the $C_{gap}$ makes an additional charging and voltage drop ($V_{gap}$=$V_G$-$V_{G1}$) prior to $C_{ox}$-induced gate charging. The $C_{gap}$ can be expressed as $A\varepsilon_0/d$, where A is the thickness of the wall area of a nanogap stripe (10 nm×20 mm), d is the gap distance, and $\varepsilon_0$ is the dielectric constant in air (or $N_2$). The $V_{gap}$ is measured from the transfer curves where an OFF-state voltage ($V_{G1}$) of the initial TFT is indicated by a dashed line of FIG. 5(a). These $V_G$ shift results may provide a key solution for sensing even an extremely low hydrogen % (in the illustrated example, 0.04%) and simultaneously for the estimation of the hydrogen %-dependent average gap distance as well. Using the $V_{gap}$ and $C_{gap}$ dependence on hydrogen %, the inventors estimated the average gap distances in 0% and 0.04% hydrogen ambiences to be about 30 nm and about 9 nm, respectively. Since the circuit is connected to the gate through the Pd TF resistor anyway if the hydrogen concentration in the chamber atmosphere is over 0.05%, the transfer curves under such conditions become almost identical to the initial transfer curve obtained without the Pd TF connection; in fact, FIG. 5(b) displays the two curves quite overlapped on the initial curve. An equivalent circuit is shown in the inset of FIG. 5(b), where the nanogap Pd TF is expressed as a variable resistor. FIGS. 5(c) and (d) are the respective illustrations of Pd TF capacitor and resistor models with diluted and concentrated hydrogen molecules in a Pd lattice.

Figure 5:
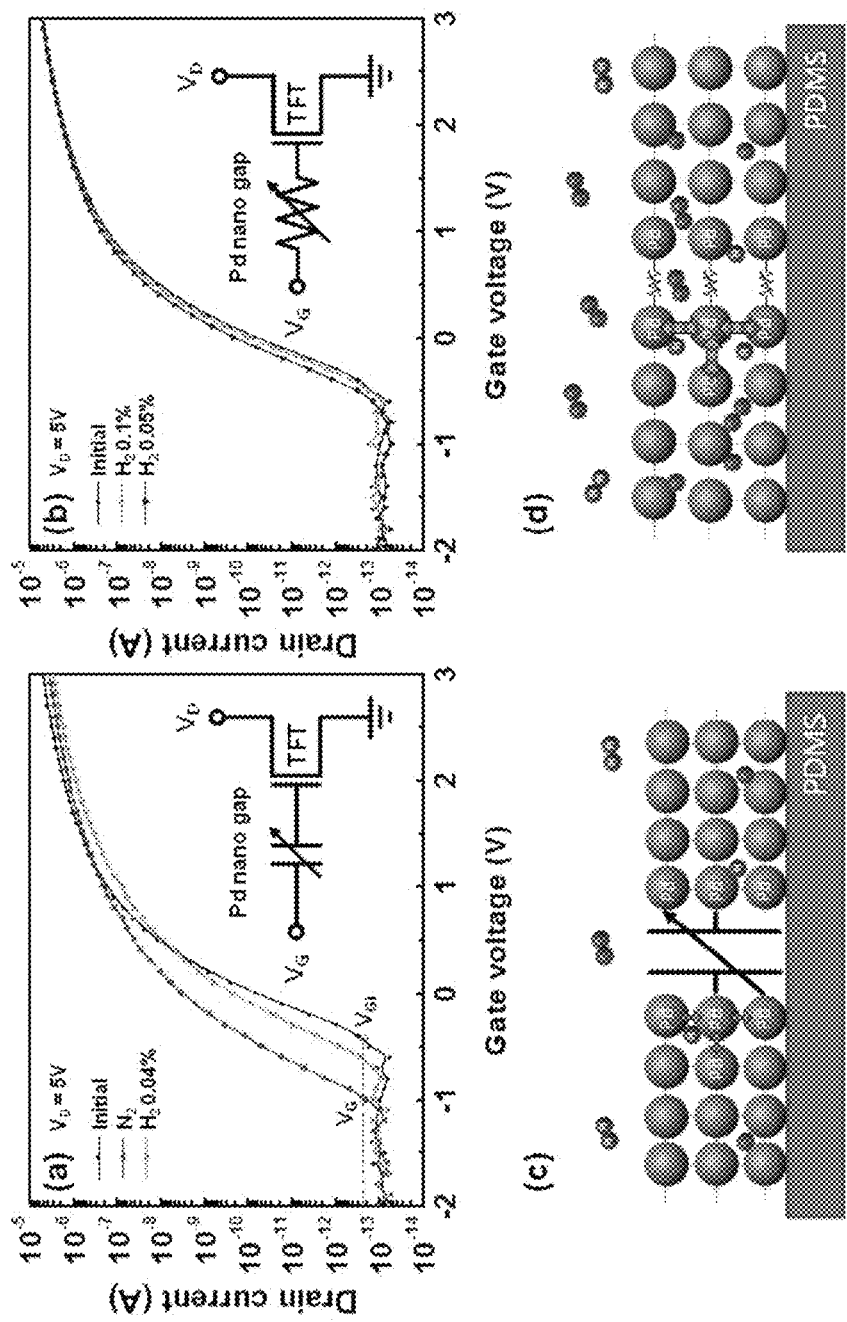
FIG. 5 shows $I_D$-$V_G$ transfer curves obtained from an initial a-IGZO TFT and from an a-IGZO TFT coupled to a Pd thin film variable capacitor, and respective models of the Pd thin film capacitor and a resistor with diluted and concentrated hydrogen molecules in a Pd lattice.

Like this, as shown in FIG. 5, the Pd hydrogen sensor connected to the a-IGZO TFT can serve as two functional elements, i.e. a variable resistor (FIG. 5A) and a capacitor (FIG. 5B). When the Pd hydrogen sensor serves as the variable resistor, the Pd sensor operates in an ON mode. In the OFF mode, a change in size of the gaps in the Pd thin film induces a change in capacitor, resulting in shifted $I_D$. Accordingly, even a low concentration of hydrogen, at which the Pd thin film is in an OFF mode, can be detected.

Figure 6:
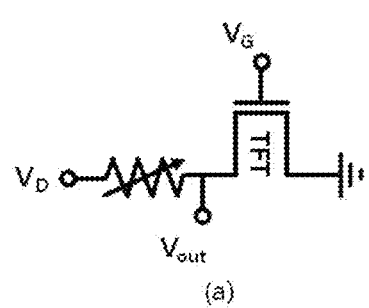
FIG. 6 is a schematic circuit diagram showing a configuration of a possible hydrogen sensor system according to an embodiment of the present invention.
Figure 6:
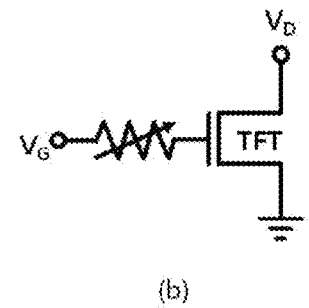
Figure 6:
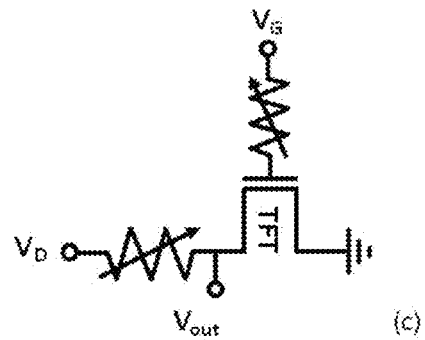

As such, according to the embodiment of the present invention, hydrogen is detected at the Pd nanogap thin film part to generate a current signal, which is in turn converted or amplified into a voltage signal in the TFT. That is, according to the inverter-type hydrogen sensor system in which the Pd nanogap thin film part is connected to the source (or drain) of the TFT, the current signal detected from the Pd nanogap thin film part is converted into the voltage signal and transformed into a complete ON/OFF mode at the same time. That is, as shown in FIG. 6(a), the hydrogen sensor in which the hydrogen-sensing unit including the Pd nanogap thin film part is connected to the source (or drain) of the TFT is referred to as an 'inverter-type hydrogen sensor' in the present invention. As described above, the inverter-type hydrogen sensor converts the current signal detected from the hydrogen-sensing unit into the voltage signal completely indicative of ON-OFF state (see e.g. FIG. 4(b)).

The present invention is not limited to the above embodiment. For example, the hydrogen-sensing unit including the Pd nanogap thin film part may be configured to be connected to the gate of the TFT, thereby forming a hydrogen sensor, which is referred to as a 'gate-type hydrogen sensor' in the present invention (see FIG. 6(b)). According to this gate-type hydrogen sensor system, the hydrogen sensor (Pd nanogap thin film part) exposed to low hydrogen concentrations serves as an accumulator so that channels are formed in the TFT, thereby detecting a low concentration of hydrogen (the size of the gap (gap distance) of the hydrogen sensor and therefore voltage applied to the gate change with the hydrogen concentrations, so that a low concentration of hydrogen can be detected). That is, since the size of the Pd gap changes at a low concentration, capacitance of the accumulator also changes (as the gap is large, the capacitance of the accumulator is small, and conversely, as the gap is small, the capacitance of the accumulator is large). Thus, although the gap exists at a low concentration hydrogen (OFF state), a voltage applied to the gate is generated due to the capacitance, resulting in $I_D$ shift. With this configuration, the hydrogen concentrations below the level which the Pd sensor can detect can also be detected.

In brief, according to an embodiment of the present invention, there is provided a hydrogen sensor system which includes a Pd nanogap thin film part serving as a hydrogen concentrations-dependant analog variable resistor and an electrically stable a-IGZO TFT. Here, when the Pd nanogap thin film part is connected to the source (or drain) of the TFT, an inverter-type hydrogen sensor circuit is formed, so that, in view of output voltage, signal visibility and signal detection rate, which are induced by hydrogen, is considerably improved, thereby providing an ability to detect approximately 0.05% hydrogen concentrations. In the meantime, when the Pd nanogap thin film part is connected to the gate of the TFT, hydrogen concentrations lower than 0.05% can be detected. This is because the Pd thin film part serves as a hydrogen-dependant variable capacitor. Thus, according to the hydrogen sensor system of the present invention, a very low concentration of hydrogen can also be detected.

Although preferred embodiments have been illustrated in the description, the present invention is not limited to the embodiments. For example, although the embodiments illustrate the hydrogen sensor system having the inverter-type, in which the hydrogen-sensing unit is connected to the source (or drain) of the TFT, and the gate-type, in which the hydrogen-sensing unit is connected to the gate of the TFT, the present invention is not limited to the embodiments. That is, as shown in FIG. 6(c), the present invention can employ a hybrid-type hydrogen sensor system in which the inverter-type and the gate-type are integrated. According to this hybrid-type hydrogen sensor system, a first hydrogen-sensing unit is connected to the gate and a second hydrogen-sensing unit is connected to the source (or drain) of the TFT. With this hybrid-type hydrogen sensor system, a lower concentration of hydrogen can be detected by means of the gate-type sensing unit, and the detected signal can be converted into a voltage signal indicative of ON-OFF state by means of the inverter-type sensing unit. That is, the above-mentioned embodiments may be modified and changed into a variety of forms within the scope of the invention defined by accompanying claims, and the modified and changed forms also belong to the scope of the present invention.

In the meantime, the embodiments are illustrated so that the hydrogen-sensing unit including the Pd nanogap thin film part is connected to the TFT in order to convert the current signal detected from the hydrogen-sensing unit into voltage. However, according to a modified embodiment, the hydrogen-sensing unit can be connected to a conventional transistor or other alternative means, rather than the TFT. As described with respect to FIG. 6(a), the inverter-type hydrogen sensor has a circuit that can control a detected voltage according to a ratio of two resistances (currents). That is, in FIG. 6(a), output voltage $V_{OUT}$ varies with the provision of the hydrogen sensor (a kind of variable resistor in which resistance changes with the hydrogen concentrations and thus the detected also changes) between $V_D$ and Vout and the resistor (stationary resistor) of the TFT, and the Vout is connected to a monitoring system so as to observe the behavior of the hydrogen sensor.

Figure 7:
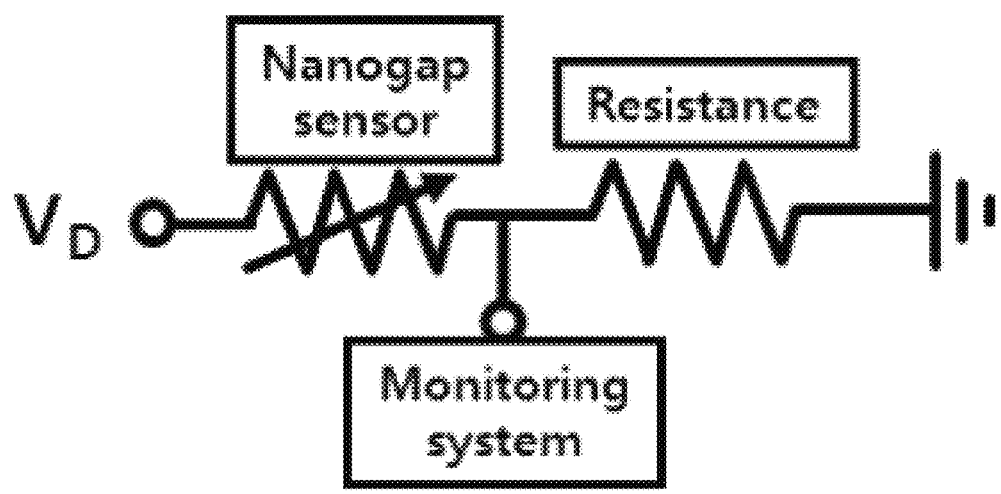
FIG. 7 is a schematic circuit diagram showing a configuration of a hydrogen sensor system according to a modified embodiment of the present invention.

According to a modified embodiment, as shown in FIG. 7, the hydrogen-sensing unit including the Pd nanogap thin film part is connected to the resistor, rather than the TFT, and Vout therebetween is connected to a monitoring system (e.g. a computer), thereby forming a hydrogen sensor.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A hydrogen sensor comprising:
a transistor;
a first hydrogen sensing unit connected to a gate of the transistor, and
a second hydrogen sensing unit connected to a source (or drain) of the transistor, wherein each of the first and second hydrogen sensing units comprises:
a substrate made of an elastic material;
a thin film made of transition metal or alloy thereof, disposed on a surface of the substrate and having a plurality of nanogaps formed therein; and an electrode formed on the thin film, and
wherein the hydrogen sensor forms a hybrid-type hydrogen sensor consisting of an inverter-type hydrogen sensor comprising the first hydrogen sensing unit and a gate-type hydrogen sensor comprising the second hydrogen sensing unit.

2. The hydrogen sensor according to claim 1, wherein the transistor comprises a thin film transistor (TFT).

3. The hydrogen sensor according to claim 2, wherein the TFT comprises an a-IGZO TFT.

4. The hydrogen sensor according to claim 3, wherein a change in current induced from a concentration of hydrogen, which is detected via the gate-type hydrogen sensor, is converted into an ON-OFF type voltage signal via the thin film transistor of the inverter-type hydrogen sensor.

5. The hydrogen sensor according to claim 2, wherein a change in current induced from a concentration of hydrogen, which is detected via the gate-type hydrogen sensor, is converted into an ON-OFF type voltage signal via the thin film transistor of the inverter-type hydrogen sensor.

\* \* \* \* \*